(12) United States Patent
Weisbuch (10) Patent No.: US 8,153,066 B2
(45) Date of Patent: Apr. 10, 2012

(54) DEVICE FOR SUPPORTING CHROMOPHORE ELEMENTS

(75) Inventor: Claude Weisbuch, Paris (FR)

(73) Assignee: Genewave, Evry (FR)

( * ) Notice: Subject to any disclaimer, the term of this patent is extended or adjusted under 35 U.S.C. 154(b) by 1475 days.

(21) Appl. No.: 11/106,247

(22) Filed: Apr. 14, 2005

(65) Prior Publication Data

US 2005/0201899 A1    Sep. 15, 2005

(51) Int. Cl.
*G01N 21/01* (2006.01)
*G01N 33/53* (2006.01)

(52) U.S. Cl. .......... 422/82.11; 422/68.1; 422/82.08; 385/129

(58) Field of Classification Search .......... 117/918; 385/129–132; 422/82.11, 68.1, 82.05, 82.08
See application file for complete search history.

(56) References Cited

U.S. PATENT DOCUMENTS

| | | | | |
|---|---|---|---|---|
| 4,970,563 A | * | 11/1990 | Gaylord et al. | 257/26 |
| 5,577,137 A | * | 11/1996 | Groger et al. | 385/12 |
| 5,717,804 A | * | 2/1998 | Pan et al. | 385/94 |
| 5,979,423 A | * | 11/1999 | Poindexter et al. | 123/697 |
| 6,137,117 A | | 10/2000 | Feldstein et al. | |
| 2002/0110839 A1 | * | 8/2002 | Bach et al. | 435/7.9 |
| 2003/0108291 A1 | * | 6/2003 | Duveneck et al. | 385/37 |

FOREIGN PATENT DOCUMENTS

FR    2 793 560    1/2000
WO    WO 02/16912    2/2002

OTHER PUBLICATIONS

Benisty, H. et al., "Optical and Confinement Properties of Two-Dimensional Photonic Crystals", *Journal of Lightwave Technology*, vol. 17, No. 11, Nov. 1999, pp. 2063-2077.

* cited by examiner

*Primary Examiner* — In Suk Bullock
*Assistant Examiner* — Paul Hyun
(74) *Attorney, Agent, or Firm* — Alston & Bird LLP (57) ABSTRACT

A device for supporting chromophore elements suitable for emitting fluorescence in response to light excitation, the device comprising a substrate having a surface layer carrying the chromophore elements, forming a planar waveguide, and containing photoluminescent constituents which emit guided luminescence at the excitation wavelength(s) of the chromophore elements when they are excited by primary excitation light illuminating the surface layer. The invention is particularly applicable to biochip type devices.

27 Claims, 5 Drawing Sheets

DEVICE FOR SUPPORTING CHROMOPHORE ELEMENTS

The invention relates to a device for supporting chromophore elements, in particular devices such as those commonly called "biochips".

BACKGROUND OF THE INVENTION

In such devices, a generally multi-layer substrate carries chromophore elements that are chemical molecules or biological molecules, dye elements added or grafted to the chemical biological molecules, or semiconductor nanostructures such as quantum boxes or wires that respond to excitation by appropriate light by emitting fluorescence at a wavelength that depends on their nature. This fluorescence makes it possible in particular to identify and find on the substrate molecules that have responded to given treatments.

Proposals have already been made in patent applications WO-A-02/16912, FR 01/15140, and FR 02/10285 in the names of the same inventors, for means enabling the excitation intensity of chromophore elements to be reinforced, and thus to reinforce the fluorescence emitted by said elements. In particular, it has been envisaged to use a guided mode for the excitation light in order to excite the chromophore elements from the evanescent portion of the guided wave, which is advantageous in terms of signal-to-noise ratio and in terms of excitation light rejection. In the known technique, it has been proposed to couple the excitation light into a guiding layer of the substrate, either by illuminating a grating formed on the surface of said guiding layer, or by eliminating an edge of the guiding layer with the excitation light.

In the first circumstance, coupling is achieved only if the excitation light reaches the grating at an angle of incidence that is very accurately determined, with said angle varying with the wavelength to be coupled. The equipment therefore needs to be set up with very great mechanical and optical accuracy. In the second circumstance, the beam illuminating the edge of the guiding layer must be of a dimension that corresponds to the effective height or width of the guided mode, which is 1 micrometer ($\mu m$) or less, and it must therefore be positioned with tolerance of less than 1 $\mu m$.

The practical difficulties associated with coupling excitation light into the guiding layer of the substrate are therefore considerable.

OBJECTS AND SUMMARY OF THE INVENTION

An object of the invention is to provide a solution to this problem that is simple and effective.

To this end, the invention provides a device for supporting chromophore elements suitable for emitting fluorescence in response to light excitation, the device comprising a substrate having a surface layer for carrying the chromophore elements and forming a planar waveguide, wherein the planar waveguide contains photoluminescent constituents suitable for emitting luminescence at the excitation wavelength(s) of the chromophore elements when said constituents are themselves excited by primary excitation light, this luminescence being guided in the planar waveguide to excite the chromophore elements.

In the device of the invention, the light for exciting the chromophore elements is generated in the planar waveguide itself, thus avoiding any problems with coupling said light into the waveguide. In addition, the excitation light is itself produced by direct (non-guided) illumination of the portion of the waveguide in which the photoluminescent constituents are to be excited, which can be done in ordinary manner with quite broad tolerance, typically greater than 10 $\mu m$.

The photoluminescent constituents of the device of the invention may be of a very wide variety of kinds and may comprise in particular polymers, organic molecules, photoluminescent ions, or quantum boxes, or they may be formed in a multilayer semiconductor heterostructure.

These photoluminescent constituents may be disposed in the planar waveguide in zones that are separated from one another and substantially adjacent to the zones for carrying the chromophore elements.

Under such circumstances, various configurations are possible: in particular, it is possible to have a zone including photoluminescent constituents between two zones for carrying chromophore elements, or else two zones containing photoluminescent constituents on either side of a zone for carrying chromophore elements, or indeed a zone containing photoluminescent constituents extending around the perimeter of the guiding layer, and one or more zones inside containing the photoluminescent constituents.

It is possible to combine these various configurations with the zones containing the photoluminescent constituents being illuminated selectively by means of the primary excitation light.

In a variant, the photoluminescent constituents may be distributed in substantially uniform manner over the entire surface of the guiding layer, in which case certain zones of said surface are illuminated selectively with the primary excitation light.

According to another characteristic of the invention, wavelength filter means are provided in the planar waveguide to eliminate from the light emitted by the photoluminescent constituents those wavelengths that are identical or close to the wavelengths of the fluorescence emitted by the chromophore elements.

This improves the signal-to-noise ratio of the fluorescence emitted by the chromophore elements and picked up by appropriate optical means.

These filter means are preferably situated between those zones of the planar waveguide that include the photoluminescent constituents and those zones that are to carry the chromophore elements.

The filter means may comprise a series of grooves formed in the planar waveguide, photonic crystals operating in the plane of the waveguide, or optical cavities formed in the plane of the waveguide by confinement between edges or photonic crystals.

In a variant, the filter means may be formed by materials included in the planar waveguide and absorbing wavelengths that are identical or close to those of the fluorescence emitted by the chromophore elements.

These absorbent constituents may be dyes of the type used in the colored filters, which have particularly low photoluminescent efficiency in the spectrum bands under consideration and which convert the unwanted guided light into heat.

In yet another variant, advantage is taken of the fact that the excitation wavelength of the chromophore elements is shorter than the wavelength of the fluorescence emitted by those elements, and filtering is performed by the planar waveguide itself, the waveguide having a guided mode cut-off wavelength that lies between the chromophore element excitation wavelength and the wavelength of the fluorescence emitted by said elements.

The device of the invention further comprises means for increasing the quantity of guided luminescence reaching the zones for carrying the chromophore elements. In particular, it is possible to reflect the guided luminescence towards said zones or to cause it to pass through said zones several times. To do this, it is possible to cover the edge of the guiding layer in a metal such as, for example aluminum, silver, gold, etc., or to incorporate reflectors in the planar waveguide, said reflectors possibly being constituted by a groove, or a periodic series of a plurality of grooves forming a reflector of the distributed Bragg reflector (DBR) type, with a reflectivity waveband centered on the excitation wavelength of the chromophore elements for the angles of incidence of the guided mode under consideration, or else a two-dimensional photonic crystal.

The production of guided luminescence from the primary excitation light can also be increased by the following means:
  a reflecting zone or layer situated under the zone or layer containing the photoluminescent constituents;
  the photoluminescent constituents can be disposed at an antinode of a vertical cavity mode in order to subject said constituents to maximum excitation intensity, with the two mirrors defining the cavity being selected to optimize conversion; or
  a photonic structure, such as cavities, formed around the zones containing the photoluminescent constituents in such a manner that said guided emission takes place in cavity modes.

It is also possible to couple the light emission of the above-mentioned constituents optimally to the guided mode by using the following means:
  the zones containing the photoluminescent constituents are situated at an anti-resonance level in vertical emission (perpendicular to the planar waveguide), thus enabling emission in a vertical direction to be reduced in favor of guided emission; or
  the zones containing the photoluminescent constituents are placed in a reflecting layer, e.g. a metallic layer, at a distance corresponding to inhibition of the excitation of the vertical modes over a wide angular range. Under such circumstances, the primary excitation light illuminates the face of the substrate opposite from the face including the above-mentioned reflecting layer.

The device of the invention may naturally include various kinds of photoluminescent constituent that emit at different wavelengths when they are excited, in order to excite the various kinds of chromophore element at different wavelengths. Under such circumstances, a single primary excitation light or a plurality of primary excitation lights having different spectrum bands can be used to excite the photoluminescent constituents.

The various photoluminescent constituents may be grouped together by kind and form distinct different regions associated with reflectors and filter means of the above-specified type.

These regions may also be superposed in the plane of the guiding layer, being disposed at different heights in said layer.

The photoluminescent constituents of different kinds may also be mixed together and spread throughout the guiding layer in proportions selected as a function of the light powers desired from each of the species.

To prevent the primary excitation light and the non-guided luminescence that might be diffused via the substrate managing to constitute a harmful background signal, an absorbent layer may be disposed over part or all of the substrate, being situated beneath the planar waveguide and consuming photons emitted from said waveguide.

In the device of the invention, it is also possible to use the means described in above-mentioned patent application FR 02/10285 in the name of the same inventors, and in particular the means relating to structures for support areas for chromophore elements that enable a useful signal to be distinguished from overall background noise.

In general, and as described in the prior patent application WO-A-02/16912 in the name of the same inventors, the fluorescence emitted by the chromophore elements can be picked up either from above the device of the invention with a lens having a given numerical aperture, or from beneath the device using a matrix of photodetectors of the charge-coupled detector (CCD) type or of the complementary metal oxide on silicon (CMOS) type and forming part of the substrate.

The invention also applies to the format of the microslides ("SBS") format, e.g. having 24, 96, 384, or 1536 wells, where the positioning of the photoluminescent elements and of the filter means is adapted to the shapes of the microslide and of the wells.

It also applies to the format of microscope slides including microwells, made by depositing a layer having a thickness of several tens of micrometers and having orifices forming the microwells (e.g. by HTC treatment of the Teflon® type sold under the trade name Cel-Line by Erie Scientific Corp., Portsmouth, N.H.). The various wells can be used as separate hybridization zones for different test samples.

The invention also relates to the use of device as specified above in a liquid medium containing chromophore elements in suspension together with diffusing particles.

In the liquid medium, only those chromophore elements that are held stationary on the surface of the device are excited by the evanescent portion of the guided wave, and not those chromophore elements that are in suspension, thereby considerably improving the signal-to-noise ratio and making it possible to measure the hybridization signal with time resolution.

BRIEF DESCRIPTION OF THE DRAWINGS

The invention will be better understood and other characteristics, details, and advantages thereof will appear more clearly on reading the following description given by way of example with reference to the accompanying drawings, in which.

MORE DETAILED DESCRIPTION

Figure 1:
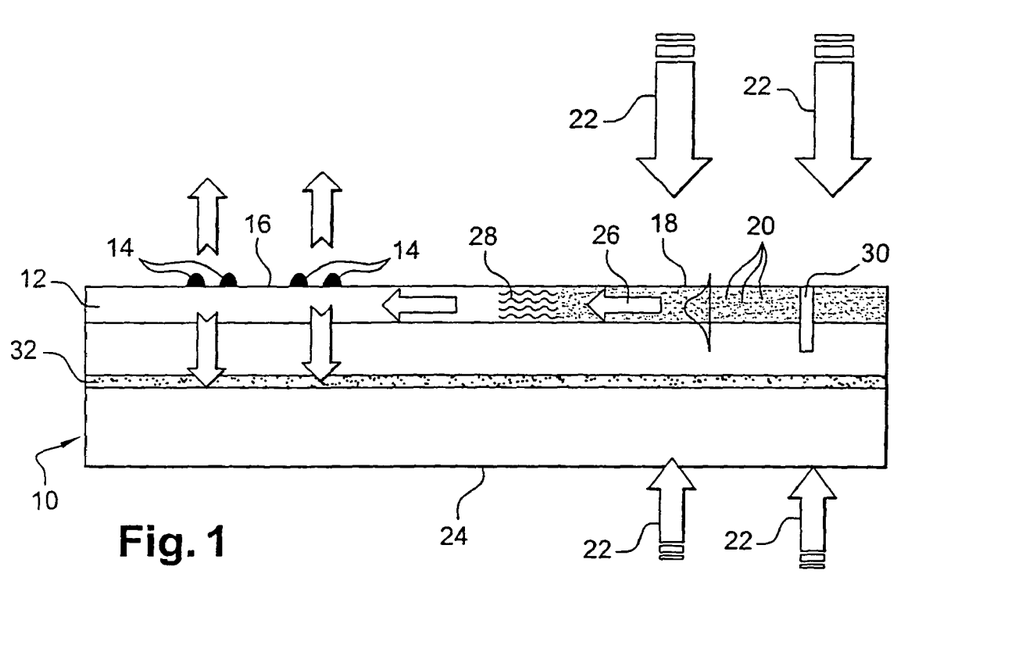
FIGS. 1 and 2 are diagrammatic section and plan views respectively of a first embodiment of a device of the invention.
Figure 2:
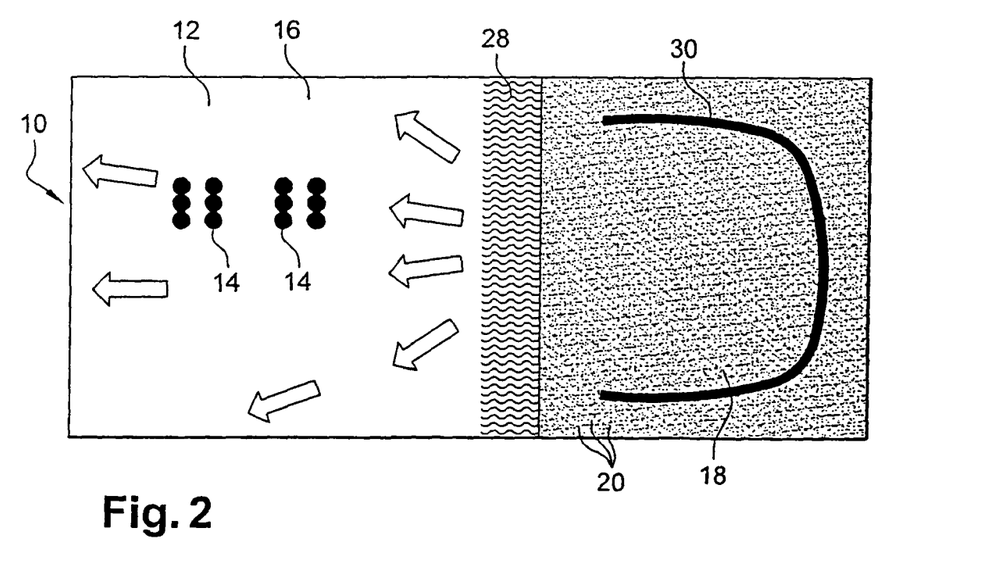

The device shown in FIGS. 1 and 2 comprises a substrate 10 of conventional type having a top layer 12 for carrying chromophore elements 14 on a portion 16 of its surface, which layer is made of a material having a high refractive index, e.g. greater than about 1.6, and forms a planar waveguide.

A portion 18 of this layer 12, adjacent to the portion 16 for carrying the chromophore elements 14, contains photoluminescent constituents 20 which emit luminescence in guided mode in the layer 12 on being excited by primary excitation light 22 directly illuminating either the portion 18 of the layer 12 containing the photoluminescent constituents 20, or the opposite face 24 of the substrate 10, as shown diagrammatically in FIG. 1.

The photoluminescent components 20 are selected, on being excited by the light 22, to emit luminescence at the excitation wavelengths for the chromophore elements 14. The chromophore elements are then excited by the evanescent portion of the guided light 26 that propagates in the layer 12.

By way of example, the layer 12 contains photoluminescent constituents 20 such as:

luminescent polymers, in particular those developed for organic light-emitting diodes (OLEDs);

organic molecules supporting a sol-gel produced silica or oxide inclusion in a polymer matrix, which inclusion may be physical or chemical (covalent bond), or electrostatic;

luminescent ions, in particular those based on transition metals or on rare earths;

quantum boxes, in particular based on II-VI or III-V semiconductors which may be chemically functionalized on their surfaces for better incorporation;

a semiconductor heterostructure comprising layers (quantum box, or wire, or well).

The photoluminescent constituents are illuminated by the primary excitation light 22 with mechanical and optical tolerance that is relatively broad, being greater than 10 μm. When the excitation wavelengths of the chromophore elements 14 are of the order of 500 nanometers (nm) to 650 nm, for example, the wavelengths of the primary excitation light 22 may lie in the range 350 nm or shorter, up to 500 nm, approximately.

The guided luminescence 26 emitted by the photoluminescent constituents 20 has a spectral band that is relatively broad because it is produced by spontaneous emission from the constituents 20, and it might include luminescence of non-zero intensity at the fluorescence wavelengths emitted by the chromophore elements 14. It is therefore necessary to filter it spectrally in order to remove therefrom any wavelengths that are identical or close to those of the emitted fluorescence, which could constitute background noise inferring with picking up the fluorescence emitted by the elements 14 (by being diffused out of the waveguide in particular via its irregularities).

For this purpose, it is possible to interpose in the layer 12, between the region 18 containing the photoluminescent constituents 20 and the region 16 carrying the chromophore elements 14, a spectral filter 28 acting on the guided luminescence 26, this filter possibly being formed by a series of grooves in the layer 12 or by photonic crystals operating in the plane, or indeed by optical cavities formed in the plane of the layer 12 by being confined between trenches or photonic crystals.

In a variant, it is possible to design the guiding layer 12 in such a manner that the cut-off wavelength of its useful guided mode (e.g. TE polarization) lies between the excitation wavelength of the chromophore elements 14 and the wavelength of the fluorescence emitted by said elements. A waveguide that is asymmetrical in terms of refractive index profile lends itself well to such operation. In this manner, the wavelengths lying between the cut-off wavelength of the guiding layer 12 and the wavelength of the emitted fluorescence are not guided by the layer 12, the light produced at said wavelengths going away from the plane of the waveguide over lateral dimensions that are small, so that the associated electromagnetic field becomes negligible in the useful zone where the chromophore elements 14 are located.

In a variant, this filtering can be implemented by the layer 12 including components that absorb at wavelengths greater longer than the excitation wavelengths of the chromophore elements 14, and in particular at wavelengths close to the wavelengths of the fluorescence emitted by said elements 14. The modal absorption coefficient of the guided mode can have a relatively high value (10 per centimeter ($cm^{-1}$) to 1000 $cm^{-1}$) without the emission from the chromophore elements 14 being affected. These absorbent components may be dyes such as those used in colored filters, having efficiency in luminescence that is particularly low in the spectral band under consideration, so as to convert the interfering guided light into heat.

Figure 3:
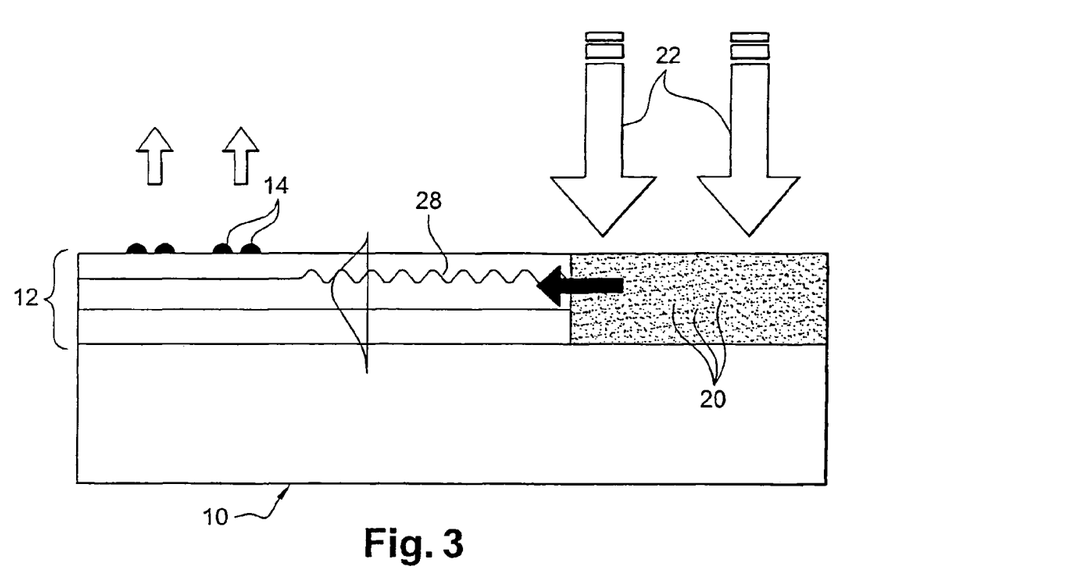
FIGS. 3 to 7 are diagrammatic section views showing variant embodiments of the device.

FIG. 3 is a diagram representing an embodiment in which the spectral filter 28 is constituted by a series of shallow grooves of sinusoidal type, for example, and/or of low index-contrast, and formed in the surface or in intermediate sublayers of the planar waveguide 12 that have different refractive indices, with the grating formed by these grooves being shown as being "buried" in the waveguide 12 in FIG. 3.

Figure 4:
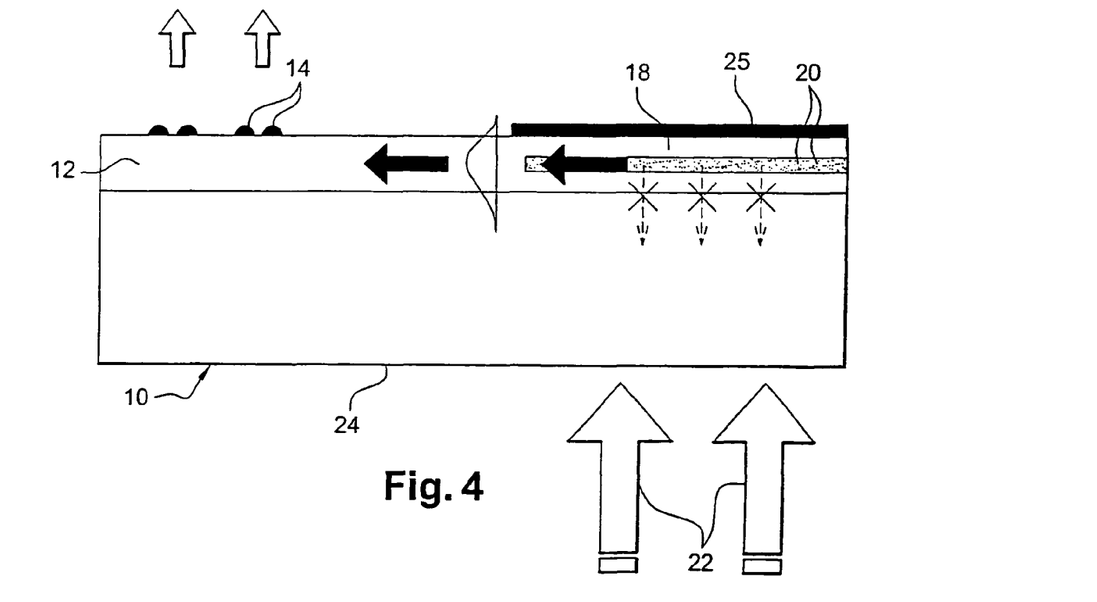

When the photoluminescent constituents 20 are illuminated by the primary excitation light 22 through the substrate 10 from its face 24 opposite from the face that is to carry the chromophore elements 14, it is advantageous for the zones 18 containing the photoluminescent constituents to be placed under a reflecting layer 25, e.g. a metal layer, located at a level that corresponds to a vertical resonance node for the emitted luminescence, as shown diagrammatically in FIG. 4.

In order to increase the quantity of guided luminescence 26 reaching the useful zone 16 that carries the chromophore elements 14, it is possible to incorporate a reflector 30 in the zone 18 of the layer 12 (see FIGS. 1 and 2), with this reflector being constituted in this example by a single groove formed through the layer 12 and forming a U-shape in the plane of this layer, the U-shape being open towards the zone 16 in order to deliver thereto a maximum quantity of guided luminescence 26. The width of the groove should typically lie in the range λ/10 to λ/3.

In a variant, this reflector may be formed by a periodic series of two or three or even more grooves forming a reflector of the DBR type having a reflectivity band at the excitation wavelength of the chromophore element 14 for the angles of incidence under consideration of the guided mode.

In another variant, the reflector may be formed by a two-dimensional photonic crystal whose forbidden bands are used in the polarizations and directions under consideration (see the article by Benisty et al., "Optical and confinement properties of two-dimensional photonic crystal", J. Lightwave Technology, Vol. 17, pp. 2063-2077, 1999).

Under all circumstances, this reflector should be formed over the entire thickness of the guiding layer 12 in order to increase its reflectivity to the guided mode. An advantage of this reflector is that it defines an appropriate curved shape for the reflecting surface that makes it possible to obtain a desired distribution for the guided luminescence (which distribution may be uniform or non-uniform) while conserving a substrate in the form of a rectangular parallelepiped. An advantage of using a two-dimensional photonic crystal is also that the diffraction effect at certain angles of incidence and at certain wavelengths makes it possible to reinforce the random nature of the distribution of the guided luminescence. Nevertheless, if a source of guided luminescence is available that delivers high power per unit area, and that is of small lateral size, i.e. of millimeter order, it is possible with a parabolic reflector 30 formed in the guiding layer 12 to obtain a guided beam that is substantially collimated and of great width (approximately 5 mm to 50 mm), which can be advantageous for subsequent processing of the guided light, in particular by means of filters. The characteristics of such filters depend on the angle of incidence of the guided mode, which leads to undesirable reflections or leaks when the light for filtering propagates over a broad range of angles of incidence.

As shown in FIG. 1, it is also possible to provide in the substrate 10, under at least a portion of the layer 12, an absorbent layer 32 that will consume all of the photons emitted from the layer 12 by diffusion of the primary excitation light 22 and/of the non-guided luminescence produced by the photoluminescent constituents 20 at the excitation wavelengths of the chromophore elements 14, where such diffuse light is liable to constitute a harmful background signal.

Figure 5:
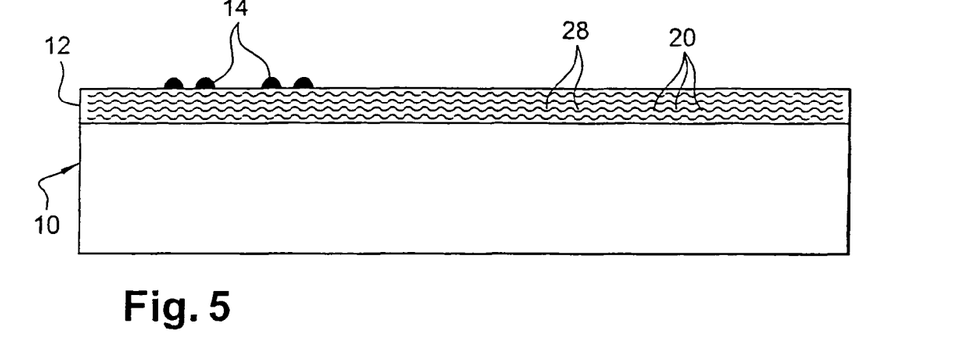

In the embodiment shown diagrammatically in FIG. 5, the guiding layer 12 of the substrate 10 carrying the chromophore elements 14 contains fluorescent constituents 20 and absorbent components (those of the filter 28 in FIGS. 1 and 2) that are mixed together and distributed in relatively uniform manner throughout the guiding layer 12.

Figure 6:
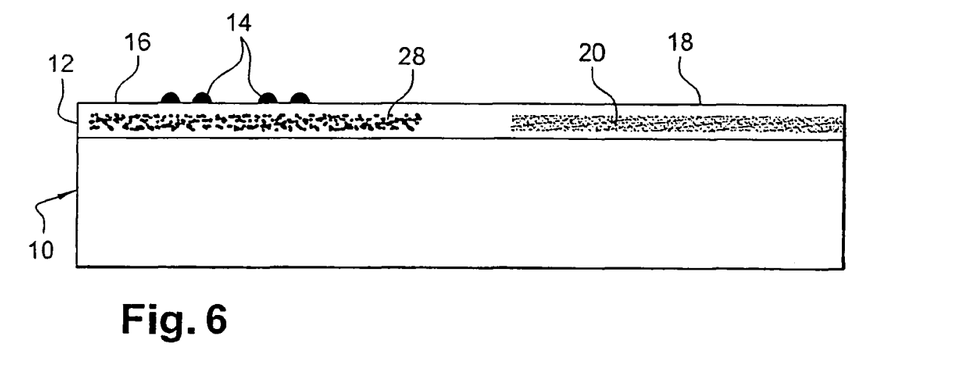

In the variant embodiment of FIG. 6, the absorbent components of the filter 28 are included in the portion 16 of the guiding layer 12 that carries the chromophore elements 14 and they form a substantially continuous layer in said region 16, while the photoluminescent constituents 20 are included in the other region 18 of the layer 12 and form a substantially continuous layer in said region.

Figure 7:
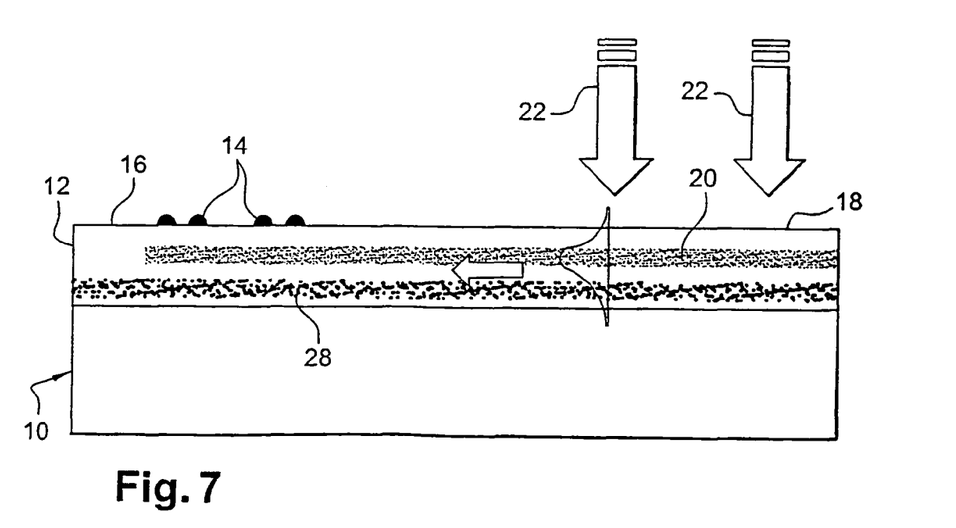

In the variant embodiment of FIG. 7, the photoluminescent constituents 20 and the absorbent components of the filter 28 form two superposed intermediate layers in the layer 12, the layer having the photoluminescent components 20 being situated directly under the chromophore elements 14 and the combination of these two layers forming a planar waveguide. The luminescence emitted by the constituents 20 is guided in this waveguide and its components at the wavelengths of the fluorescence emitted by the elements 14 are absorbed by the layer 28.

Figure 8:
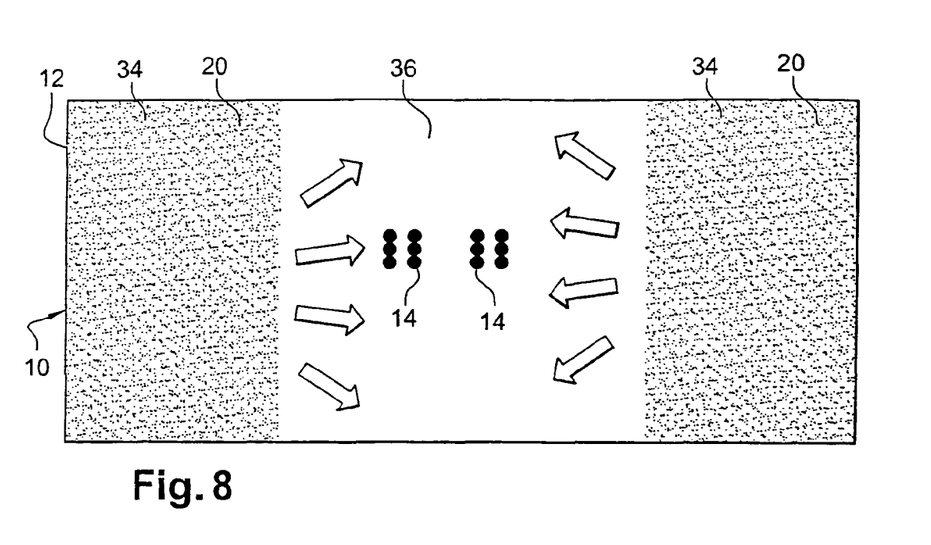
FIGS. 8 and 9 are diagrammatic plan views showing other variant embodiments of the device of the invention.

In yet another variant embodiment shown in FIG. 8, the photoluminescent constituents 20 may be grouped together in the plane of the guiding zone 12 into zones 34 that are situated on both sides of a central zone 16 carrying the chromophore elements 14.

In a variant, it would naturally be possible to use the opposite configuration, i.e. a central zone having the photoluminescent constituents 20 and two lateral zones carrying the chromophore elements 14 situated on either side of the central zone.

Figure 9:
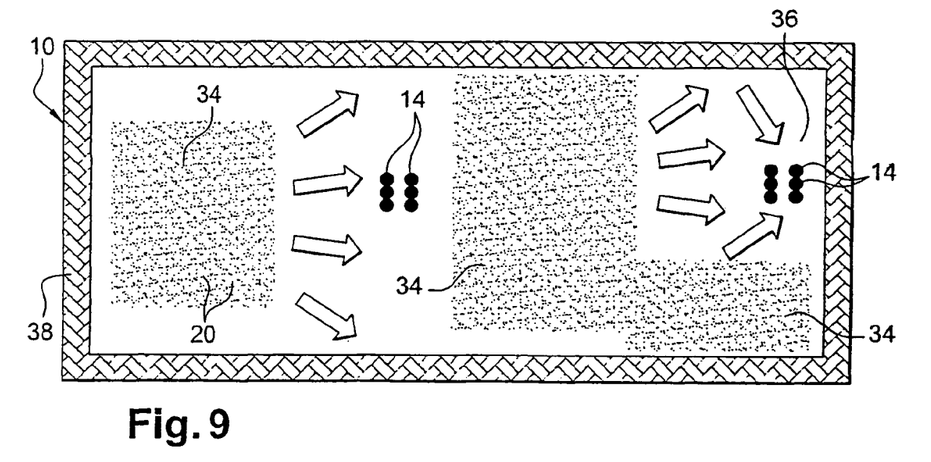
Figure 10:
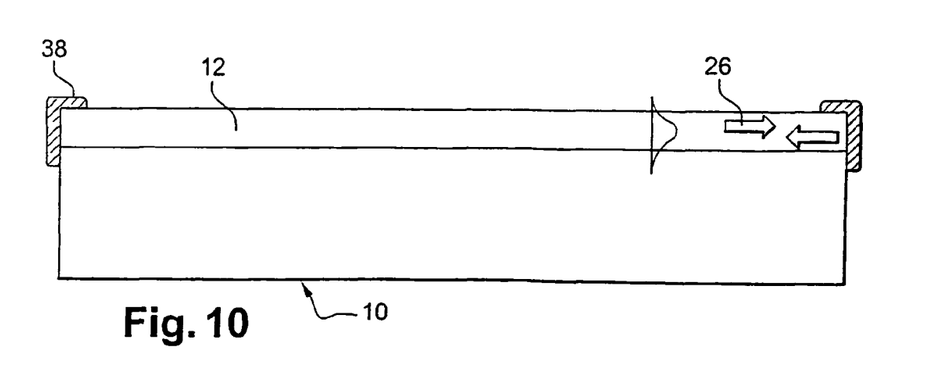
FIG. 10 is a diagrammatic section view of the FIG. 9 device.

In the variant embodiment of FIGS. 9 and 10, there can be a disposition in which the zones 34 containing the photoluminescent constituents 20 and the zones 36 carrying the chromophore elements 14 are surrounded by a reflector 38 formed by a metal coating on the edge of the guiding layer 12 around its entire periphery. This metal coating is made, for example, out of aluminum, silver, gold, etc., and it prevents light from escaping through the edge of the layer 12.

In general, only those portions of the layer 12 that include zones 34 with photoluminescent constituents should be illuminated by the primary excitation light 22. When these photoluminescent constituents are distributed over the entire layer 12, as for the embodiments of FIGS. 5 and 7, only certain portions of the layer 12 are illuminated by the primary excitation light 22, as shown diagrammatically in FIG. 7.

Figure 11:
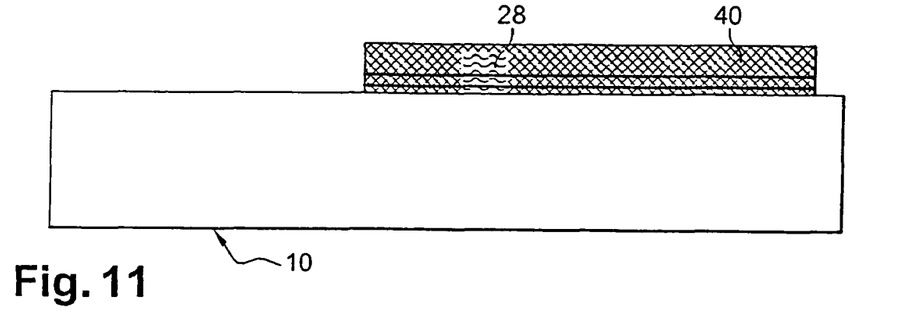
FIGS. 11 and 12 are diagrammatic section views showing two steps in making a device of the invention.
Figure 12:
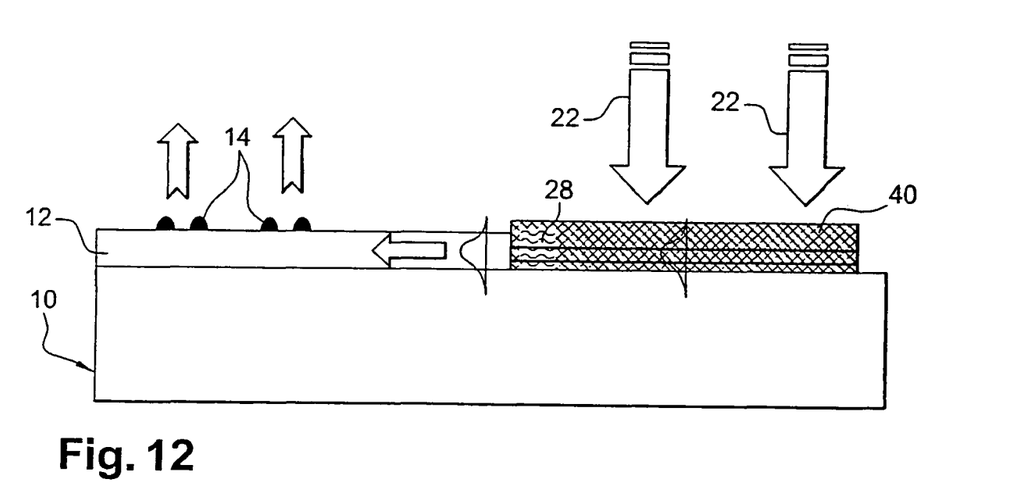

In the embodiment of FIGS. 11 and 12, the substrate 10 carries a semiconductor heterostructure 40 which constitutes a waveguide and includes an incorporated filter 28 and luminescence wells which are included in a portion of said structure 40. These wells are advantageously formed on a portion only of the heterostructure by an improved growth method such as that known under the name selective area growth (SAG) which makes it possible to avoid any reabsorption beyond said portion.

In a variant, a semiconductor film can be deposited on the substrate 10 and then cut by conventional lithographic methods so as to leave only those locations remaining that will actually be illuminated by the primary excitation light. FIG. 11 is a diagram showing the first step prior to cutting.

The guiding layer 12 is then formed on the substrate 10 (FIG. 12), e.g. by a "lift-off" method, with said guiding layer 12 being optically coupled with the structure 40 or with the above-mentioned semiconductor film.

Figure 13:
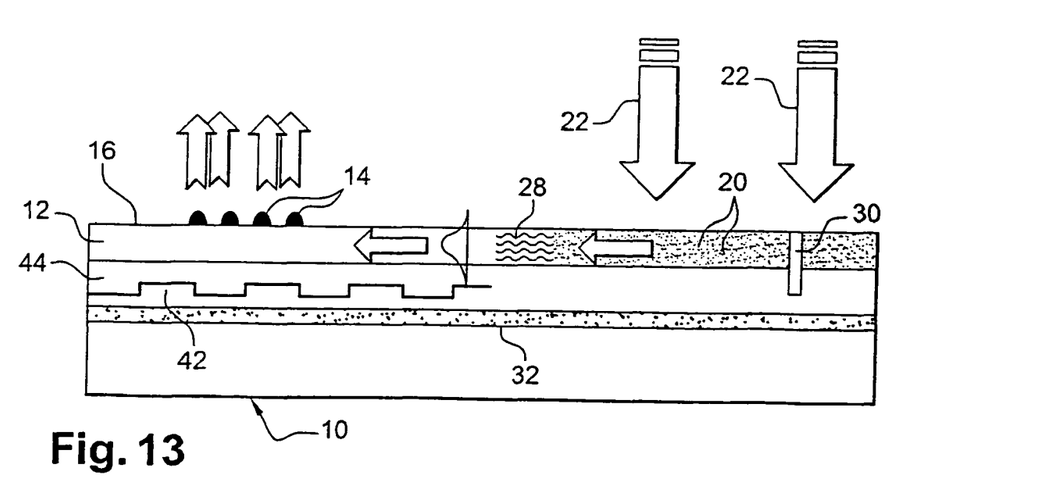
FIG. 13 is a diagrammatic section view showing another variant embodiment of the device of the invention.

In the variant embodiment of FIG. 13, the structure shown corresponds substantially to that of FIGS. 1 and 2, but the substrate 10 further comprises, beneath the zone 16 carrying the chromophore elements 14, a structured intermediate layer 42 which is partially or totally reflective for the fluorescence emitted by the chromophore elements 14 and which is disposed between the absorbent layer and the guiding layer 12, and which includes zones of different thickness or heights making it possible by destructive or constructive interference to vary the intensity of the fluorescence emitted by the chromophore elements 14. This intermediate layer 42 is covered in a layer 44 of sufficient thickness to ensure that the mode guided by the layer 12 has an evanescent field in the structured layer 42 that is negligible, so as to avoid disturbing the propagation of the guided mode.

The device of the invention may include photoluminescent constituents 20 which, on being excited, emit at different wavelengths to excite chromophore elements 14 of different types. These different constituents 20 may be mixed together or they may be separated in different zones 34.

Numerous modifications can be made to the embodiments described and shown: for example, the photoluminescent constituents 20 may form a very thin layer deposited on the surface of a pre-existing guiding layer, thus making it possible in said layer to pick up the luminescence guided by the evanescent portion of the guided mode, or to localize the layer of the constituents 20 so as to encourage the above-mentioned effects of vertical anti-resonance for the guided luminescence and of vertical resonance for the primary excitation light.

When the fluorescence emitted by the chromophore elements is picked up a matrix of CCD or CMOS photodetectors, it is advantageous to provide means for filtering the primary excitation light and/or the guided luminescence while passing at least a major fraction of the emitted fluorescence.

These filter means may be formed by one or more absorbent layers and/or by a multilayer interference filter (e.g. a properly centered Bragg mirror).

What is claimed is:

1. A device for supporting chromophore elements suitable for emitting fluorescence in response to light excitation, the device comprising a substrate having a surface layer carrying the chromophore elements and forming a planar waveguide, wherein the planar waveguide contains photoluminescent constituents suitable for emitting luminescence at the excitation wavelengths of the chromophore elements when said constituents are themselves excited by primary excitation light, the emitted luminescence being guided in the planar waveguide to excite the chromophore elements, and further wherein wavelength filter means are provided in the planar waveguide to eliminate the luminescence emitted by the photoluminescent constituents at wavelengths that are identical or close to the wavelengths of the fluorescence emitted by the chromophore elements.

2. A device according to claim 1, wherein the photoluminescent constituents comprise in particular: polymers, organic molecules, luminescent ions, or quantum boxes, or they are formed in a layered semiconductor heterostructure.

3. A device according to claim 1, wherein the photoluminescent constituents are excited by the primary excitation light illuminating the planar waveguide or the face of the substrate opposite from its face including the planar waveguide.

4. A device according to claim 1, wherein the photoluminescent constituents are disposed in the planar waveguide in separate zones substantially adjacent to the zones for carrying the chromophore elements.

5. A device according to claim 1, wherein the filter means are situated in the zones for carrying the chromophore elements.

6. A device according to claim 1, wherein the filter means are situated between the zones including the photoluminescent components and the zones for carrying the chromophore elements.

7. A device according to claim 1, wherein the filter means are constituted by series of grooves, by photonic crystals, or by optical cavities formed in the planar waveguide.

8. A device according to claim 7, wherein the grooves of the filter means have low index contrast or are of shallow sinusoidal shape, and are formed on the surface or in intermediate sublayers of the planar waveguide.

9. A device according to claim 1, wherein the filter means comprise materials included in the planar waveguide that are absorbent at wavelengths that are identical or close to those of the fluorescence emitted by the chromophore elements.

10. A device according to claim 1, wherein, since the excitation wavelength of the chromophore elements is shorter than the wavelength of the fluorescence emitted by said elements, the filtering is performed by the planar waveguide itself, said waveguide having a cut-off wavelength for its guided mode that lies between the excitation wavelength of the chromophore elements and the wavelength of the fluorescence emitted by said elements.

11. A device according to claim 1, wherein the photoluminescent constituents are distributed in substantially uniform manner within the planar waveguide.

12. A device according to claim 1, wherein the planar waveguide contains different photoluminescent constituents emitting luminescence at different wavelengths in order to excite chromophore elements of different types.

13. A device according to claim 12, wherein the different photoluminescent constituents are mixed together in the planar waveguide.

14. A device according to claim 12, wherein the photoluminescent constituents of a given type emitting at a given wavelength are separate from other photoluminescent constituents emitting on different wavelengths.

15. A device according to claim 14, wherein the photoluminescent constituents of different types are in different zones of the planar waveguide, or are in different superposed layers of the waveguide.

16. A device according to claim 1, wherein, beneath at least a portion of the planar waveguide, the substrate includes a layer of material absorbing the photons emitted from the waveguide at the wavelengths of the primary excitation light and/or of the excitation light for the chromophore elements.

17. A device according to claim 1, wherein, beneath a zone of the planar waveguide for carrying chromophore elements, the substrate includes a structured intermediate layer that reflects at least part of the fluorescence emitted by the chromophore elements and that includes zones of different thicknesses or heights enabling the intensity of said fluorescence to be caused to vary by destructive or constructive interference.

18. A device according to claim 1, wherein, in the vicinity of at least one zone containing photoluminescent constituents, the planar waveguide includes reflector-forming means for guiding the emitted luminescence towards at least one zone for carrying chromophore elements.

19. A device according to claim 18, wherein the reflector-forming means comprise a reflective coating formed on the edge of the planar waveguide, or grooves formed in the planar waveguide, or two-dimensional photonic crystals formed in the planar waveguide.

20. A device according to claim 1, wherein, beneath the planar waveguide containing the photoluminescent constituents, the substrate includes a layer of material that is reflective at the wavelengths of the emitted luminescence.

21. A device according to claim 1, wherein the planar waveguide includes resonant cavities formed by reflective layers placed on either side of the photoluminescent constituents.

22. A device according to claim 21, wherein the photoluminescent constituents are placed at the level of a vertical resonance node for the emitted light.

23. A device according to claim 21, wherein the photoluminescent constituents are excited by the primary excitation light illuminating the planar waveguide or the face of the substrate opposite from its face including the planar waveguide, and the photoluminescent constituents are placed at the level of a vertical resonance antinode for the primary excitation light.

24. A device according to claim 1, wherein the photoluminescent constituents are placed under a reflective layer at a level corresponding to a vertical resonance node for the emitted luminescence, and are illuminated by the primary excitation light through the face of the substrate opposite from its face including said reflective layer.

25. A device according to claim 1, wherein the photoluminescent constituents are placed in a thin layer on a guiding layer of the substrate.

26. A device according to claim 1, wherein the photoluminescent constituents are formed in a multilayer semiconductor structure secured to the substrate and optically coupled to a guiding layer deposited on the substrate for the purpose of carrying the chromophore elements.

27. A device according to claim 1, wherein its surface layer is covered in a layer having a thickness of several tens of micrometers, including orifices forming microwells for receiving samples.

* * * * *